United States Patent
Montano et al.

(10) Patent No.: US 7,888,463 B2
(45) Date of Patent: Feb. 15, 2011

(54) MODULATORS OF ANTIESTROGEN PHARMACOLOGY

(75) Inventors: Monica Montano, Shaker Heights, OH (US); Amelia Sutton, Birmingham, AL (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 12/275,722

(22) Filed: Nov. 21, 2008

(65) Prior Publication Data

US 2009/0143297 A1 Jun. 4, 2009

Related U.S. Application Data

(62) Division of application No. 09/972,032, filed on Oct. 5, 2001, now Pat. No. 7,459,543.

(60) Provisional application No. 60/238,190, filed on Oct. 5, 2000.

(51) Int. Cl.
*C07K 14/00* (2006.01)
(52) U.S. Cl. .................................... 530/324
(58) Field of Classification Search .................. 530/324
See application file for complete search history.

(56) References Cited

PUBLICATIONS

GenBank Accession No. AC004975, Dec. 21, 1999.
GenBank Accession No. AP004241, Nov. 6, 2001.
GenBank Accession No. AL353626, Jun. 22, 2001.
GenBank Accession No. AC012377, May 18, 2001.
GenBank Accession No. AC019184, May 9, 2001.
Bonaldo, B.F. et al., "Normalization and Subtraction: Two Approaches to Facilitate Gene Discovery," Genome Research, Sep. 1996, vol. 6 No. 9, p. 791-806.
Lazennec G. et al., "Mechanistic Aspect of Estrogen Receptor Activation Probed with Constitutively Active Estrogen Receptors: Correlations with DNA and Coregulator Interactions" Mol. Endo. vol. 11, No. 9, p. 1375-1386 (1997).
Hall, et al., "Allosteric Regulation of Estrogen Receptor Structure, function and Coactivator Recruitment by Different Estrogen Response Elements," Mol. Endo. Mar. 2002 vol. 16, p. 469-486.
Fan et al., "The Activating Enzyme of NEDD8 Inhibits Steroid Receptor Function," Mol. Endo Feb. 2002, vol. 16 No. 2, p. 315-330.
Beato et al., "Steroid hormone receptors: many actors in search of a plot," Cell, 83, p. 851-7 (1995).
Katzenellenbogen et al., "Antiestrogens: mechanisms and actions in target cells," J. Steroid Biochem Mol. Biol. 53, p. 387-93 (1995).
Tsai and O'Malley, "Molecular mechanisms of action of steroid/thyroid receptor superfamily members.," Ann. Rev. Biochem., 63, p. 451-86 (1994).
Osborne et al., "The value of estrogen and progesterone receptors in the treatment of breast cancer," Cancer, 46, p. 2884-8 (1980).
Osborne et al., "Selective estrogen receptor modulators: structure, function, and clinical use," J. Clin. Oncol. 18, p. 3172-86 (2000).
Crawford et al., "Stability of oestrogen receptor status in sequential biopsies from patients with breast cancer," Br. J. Cancer, 56, p. 137-40 (1987).
Li et al., "Estrogen and progesterone receptor concordance between primary and recurrent breast cancer," J. Surg. Oncol. 57, p. 71-7 (1994).
Response dated Feb. 3, 2005 to Office Action dated Sep. 3, 2004 for U.S. Appl. No. 09/972,032, filed Oct. 5, 2001.
Response dated Apr. 23, 2008 to Final Office Action dated Feb. 27, 2008 for U.S. Appl. No. 09/972,032, filed Oct. 5, 2001.

*Primary Examiner*—Stephen L Rawlings
*Assistant Examiner*—Brad Duffy
(74) *Attorney, Agent, or Firm*—Calfee, Halter & Griswold LLP

(57) ABSTRACT

A protein, designated ERCoA3 is provided. The ERCoA3 protein interacts with the estrogen receptor and the progesterone receptor and causes activation of these receptors is provided. Also provided are polynucleotides which encode ERCoA3 or block translation of the mRNA which encodes ERCoA3. Antibiodies that bind to one or more epitopes in the human ERCoA3 protein are provided. The present invention also relates to methods of inhibiting or reducing tamoxifen or estrogen induced proliferation of cancer cells, particularly breast cancer cells, endometrial cancer cells and uterine cancer cells. The method comprises reducing the activity or levels of ERCoA3 in such.

7 Claims, 9 Drawing Sheets

Fig. 1

GGAATTGTTCTCGAGGCCAAGAATTCGGCAAGGCCGATCTCCTGACCTCGTGATCCGCCC
GCCTCAGCTTCCCAAAGTCTGGGATTACAGGCATGAGCCACCGCGCCCGCCCCCCGAC
ACCTAGTTTAAAGGGCCCCTGCTGTGTCCGCGCTGCCGCCGCTCCCCAGCTGCCCAGT
CTGGCGGGCTCAGTCCCGCGTTGCCATGTGTGGGAGACCGCGTCGCGTAAGCGCTGGAT
GTGGCTTCGCTGATGCACATTGGACACCGGGCTCTGGACTGGGCTAGGGAAGGCAGGAG
GGCGGAATTGGGCCCGAGGCCCCCCGGTTGGCCCCAGGCGCCCTCCGCGCCTCCGGTGCC
CCGCAGCGCGCCCCCCGGTGGCTCCGGGAGTGCAGGTCTTACCGTCCGAGATCGTCCGCAAC
TGGGCGAGCTGTGCATGGGCGTGGCTAAGGCCCGTGGTTTGTTACGATTGGCCAGCGG
GACTTAAGTGTGTTGTCTCTGAAGAGCATGGCGCTTAGGTCTAGGAAGCGGGTCTGTGGGGCCTTA
TCCCCGCCCACCATCAAATGGGCCAGAGACATACCGGAAGTGGTTGGATTGTATACCGGATCG
GGGCGAGGCGCAGAGACACTGGAAGAGCTCCACCTTCTTGGACTGTGCAGATGCCCCGGCAATCCAGTGTGT
AACCCCCAAAGAGACACTGGAAGAGCTCCACCTTCTTGGACTGTGCAGATGCCCCGGCAATCCAGTGTGT
CGTGGGCTTTACAGGGAAAGAGCTGCCCACCTTCTCTGCTTGCAGATGCTGCCATCTAGGTGT
GTCCACCCGATGGGAGCTCCCTGATTCTCTGCTTCCCAGTACAAAGTCGATTTGG
ACCTGGGCCTGCCTTCCATCCACTCCTCTGCCTTCAGAGTAAAATTGCAAGATCT
GTTGGTGCAAAAAAAAAAAAAAAAAAAAAATGAGCGGCCCGCAAGTT

Fig. 2

MCGRPRRVSAGCGFADAHWTGLWTGLGEGQEGGIGPEGQASPTPDCASRWPRSASRWPW
SAGLTVRDRPQLGELCMGRG

Fig. 3
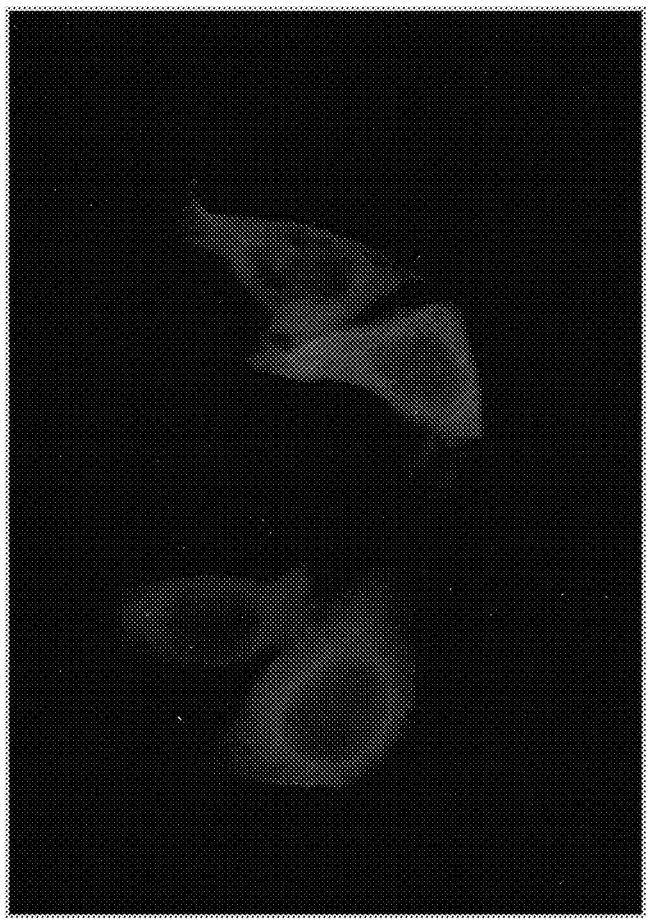
GFP-PCMT
GFP-ERCoA3

Fig. 6
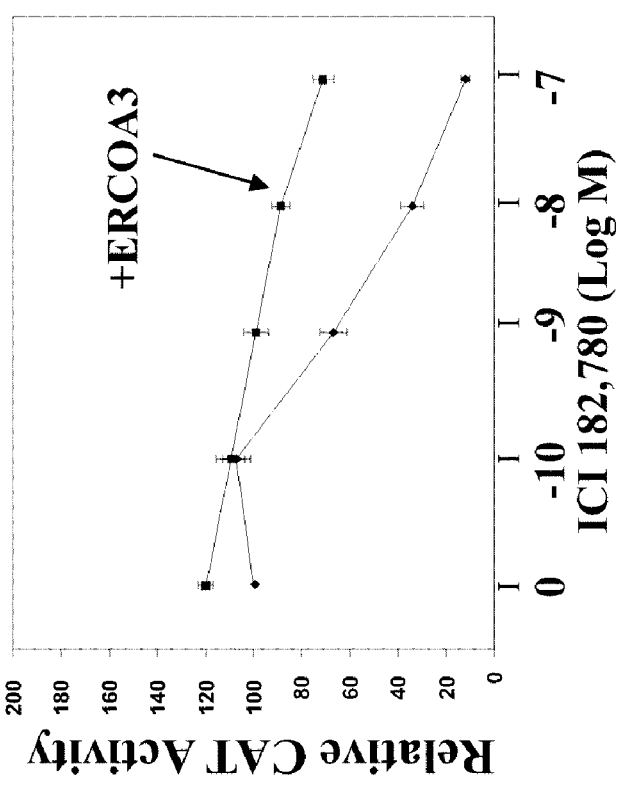
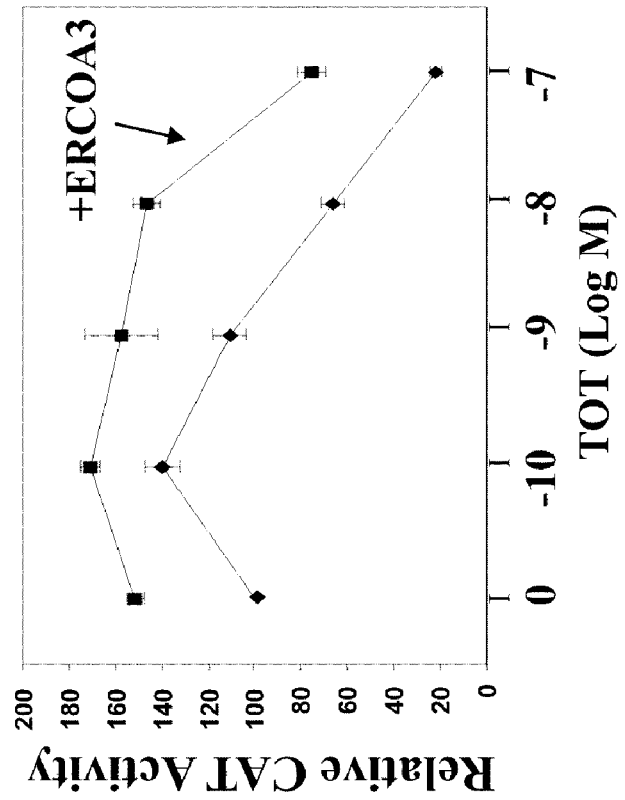

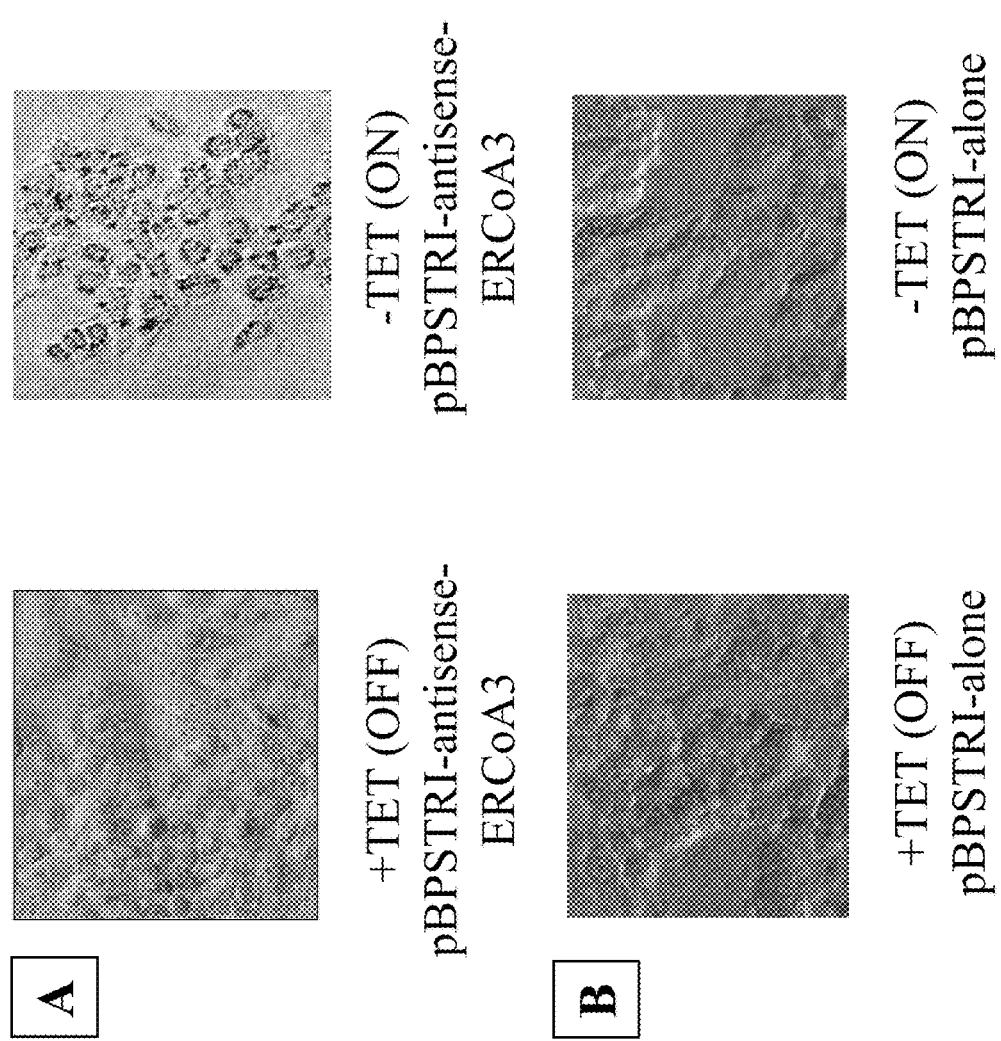

SEQUENCE LISTING

```
<160> NUMBER OF SEQ ID NOS: 4

<210> SEQ ID NO 1
<211> LENGTH: 990
<212> TYPE: DNA
<213> ORGANISM: Homo sapiens

<400> SEQUENCE: 1
ggaattgttc tcgaggccaa gaattcggca aggcgatctc ctgacctcgt gatccgcccg        60
cctcagcttc ccaaagtgct gggattacag gcatgagcca ccgcgccgg ccccgacac        120 ctagttttaa agggcccctg ctgttgctgc cgctgccgcc gctcccagct gcccagtctg       180
gcgggctcag tcccgcgttg ccatgtgtgg gagaccgcgt cgcgtaagcg ctggatgtgg       240
cttcgctgat gcacattgga ccgggctctg gactgggcta ggggaagggc aggagggcgg       300
aattgggccc gagggccagg cctcgccgac ccccgactgc gcctcccggt ggccccgcag       360
cgcctcccgg tggccctgga gtgcaggtct taccgtccga gatcgtccgc aactgggcga       420
gctgtgcatg gggcgtggct aaggccgtgg tttggttacg attggccagc gggacttaag       480
tgttgtctct gaagagcatg gacattagtc tggagggtcc tggaagagtg atccccgccc       540
```

-continued

```
caccatcaaa tggcgcttag gtctaggaag cgggtgtggg tggggcctta gggcgaggcg      600
cagacatacc ccgaagtggt tggattgtat accgcaaggg gctggatcga accccccaaa      660
gacactggaa ggctgtgtgg ctgaggaggg cccggcaatc cagtgtgtcg tgggctttac      720
aggaaagagc tccaccttct tggagtgtgc agatgcgatc taggtgtgtc cacccgatgg      780
gagctgcggg ccgggcagat gctgcccag tacaaagctg atttggacct ggggcctctg      840
gacttccctg attctctgct tgcatctcca gcaaagtcct gtcccgttgg ctgccttcat      900
ccactctctc acttctctgc cttcagagta aaattgcaag atctgtggtg caaaaaaaaa      960
aaaaaaaaaa aaaatgagcg gccgcaagtt                                       990
```

<210> SEQ ID NO 2
<211> LENGTH: 79
<212> TYPE: PRT
<213> ORGANISM: Homo sapiens

<400> SEQUENCE: 2

```
Met Cys Gly Arg Pro Arg Arg Val Ser Ala Gly Cys Gly Phe Ala Asp
1               5                  10                  15

Ala His Trp Thr Gly Leu Trp Thr Gly Leu Gly Glu Gly Gln Glu Gly
                20                  25                  30

Gly Ile Gly Pro Glu Gly Gln Ala Ser Pro Thr Pro Asp Cys Ala Ser
            35                  40                  45

Arg Trp Pro Arg Ser Ala Ser Arg Trp Pro Trp Ser Ala Gly Leu Thr
        50                  55                  60

Val Arg Asp Arg Pro Gln Leu Gly Glu Leu Cys Met Gly Arg Gly
65                  70                  75
```

<210> SEQ ID NO 3
<211> LENGTH: 20
<212> TYPE: DNA
<213> ORGANISM: Homo sapiens

<400> SEQUENCE: 3

```
ggaattgttc tcgaggccaa                                                  20
```

<210> SEQ ID NO 4
<211> LENGTH: 20
<212> TYPE: DNA
<213> ORGANISM: Homo sapiens

<400> SEQUENCE: 4

```
aacttgcggc cgctcatttt                                                  20
```

MODULATORS OF ANTIESTROGEN PHARMACOLOGY

CROSS REFERENCE TO RELATED APPLICATIONS

This application is a divisional of, claims priority to, and any other benefit of, U.S. patent application Ser. No. 09/972,032, filed on Oct. 5, 2001, and entitled MODULATORS OF ANTIESTROGEN PHARMACOLOGY, and claims priority to, and any other benefit of U.S. Provisional Patent Application Ser. No. 60/238,190, filed Oct. 5, 2000, both of which are hereby incorporated in their entirety.

This invention was made, at least in part, with government support under National Institutes of Health Grant No. R29CA080959. The U.S. government has certain rights in the invention.

BACKGROUND

Estrogens are steroid hormones that are essential for normal sexual development and functioning of female reproductive organs. Estrogens are also important for growth, differentiation, and functioning of the testis, epididymis and prostate in males. Estrogens also have important non-reproductive effects on bones and the heart. Estrogens comprise a group of natural and synthetic substances. Natural estrogens include estradiol (i.e., 17-β-estradiol or E2), estrone and estriol. Estrogens are sometimes given therapeutically in the form of a conjugate, such as for example, ethinyl estradiol, conjugated estrogens or diethylstilbestrol.

Tissues in the body that are responsive to estrogens are called "estrogen-sensitive" or "estrogen-responsive" tissues and include cells of the urogenital tract, cardiovascular system and skeletal system. The cells that comprise estrogen-sensitive tissues contain estrogen receptors (ER). ER can be of the α type or β type. Estrogens enter cells and bind to ER in the cytoplasm of such cells and an estrogen-ER complex is formed. Herein, a molecule such as estrogen that binds to a receptor is generally called a "ligand." Herein, a receptor such as ER that has formed a complex with a ligand is called a "liganded" receptor.

Once the estrogen ligand binds to ER, the estrogen-ER complex migrates to the nucleus of the cell and binds to specific sequences of DNA within the cellular genome called "estrogen response elements." Such estrogen response elements are located in the promoters of specific genes in the cell nucleus.

Binding of the estrogen-ER complex to estrogen-responsive elements causes activation or suppression of the transcription of the specific genes (Beato, et al., 1995, Cell, 83:851-7; Katzenellenbogen, et al., 1995, J Steroid Biochem Mol Biol, 53:387-93; Tsai and O'Malley, 1994, Annu Rev Biochem, 63:451-86). The activation or suppression of specific gene transcription is one type of molecular and/or cellular response that can result from formation of a ligand-receptor complex. When such a response occurs, the receptor is said to have been "activated."

Estrogen-ER complexes, therefore, act as transcription factors to regulate the expression of these genes. When a ligand binds to a receptor and a molecular and/or cellular response (e.g., transcriptional regulation of genes) occurs, such ligands are referred to as "agonists" and the response produced is called "agonism." Herein, therefore, the term agonist refers to ligands, such as estrogen, that produce the molecular and/or cellular responses.

In addition to the role estrogens and ER play in normal development and functioning of cellular tissues, estrogens and ER play significant roles in certain human disease states, breast cancer being one specific example. Cells in female breast tissue normally contain ER. Interaction of estrogens with ER in breast cells normally causes the breasts to grow at puberty and again during pregnancy. Since breast cells normally contain ER, it is not surprising that cells comprising tumors of the breast also contain ER. Ninety-five percent of all breast tumors, at least initially, have ER and are dependent on estrogens for growth. In such breast tumor cells, estrogens acting via the ER, dramatically escalate proliferative and metastatic activity (Osborne, et al., 1980, Cancer, 46:2884-8).

Treatment of such ER-positive breast tumors comprises administration to the individual with the tumor, compounds such as tamoxifen (TOT). TOT can also administered to individuals who may be at high risk for developing breast tumors in the future, for the purpose of prevention of such tumors. Chemically, tamoxifen is one of a number of compounds referred to as triphenyethylene derivatives. Tamoxifen is a mainstay of breast cancer treatment and inhibits the proliferation promoting effect of estrogens (Katzenellenbogen, et al., 1995, J Steroid Biochem Mol Biol, 53:387-93; Osborne, et al., 1980, Cancer, 46:2884-8; Jordan and Murphy, 1990, Endocr Rev, 11:578-610). Like estrogens, TOT binds to ER and, therefore, is also an ER ligand. Unlike estrogen binding to ER, however, TOT binding to ER does not result in production of significant molecular and/or cellular responses. The changes in gene expression resulting from TOT binding to ER are significantly less in magnitude than those resulting from estrogen binding to ER. Such decreased responses are referred to as "partial agonism." Ligands such as TOT, that result in partial agonism, are referred to as "partial agonists."

Of significance is that binding of ER by TOT prevents estrogens from producing their effect on ER (i.e., the partial agonist precludes effects of the agonist). Since estrogens are prevented from producing a molecular and/or cellular response through the ER, the response produced in the presence of both estrogens and TOT will be partial agonism, rather than agonism. Such partial agonism is the basis by which TOT impairs breast tumor growth (i.e., by blocking the agonist effects of estrogens).

In addition to partial agonists like TOT, other substances exist that bind ER but then produce no molecular and/or cellular response. Such substances are referred to as "antagonists." One such antagonist is ICI182,780 (ICI). ICI binding to ER prevents estrogens from binding to ER. Therefore, like TOT, ICI also impairs proliferation of ER-positive breast tumor cells caused by estrogen.

Substances that bind to the ER and prevent the molecular and/or cellular responses caused by estrogens are given the general name "selective estrogen receptor modulators" or SERMs (Osborne, et al., 2000, J Clin Oncol, 18:3172-86). SERMs can also be called "antiestrogens." SERMs encompass ER ligands that produce different responses. For example, one particular SERM may be an antagonist. Another particular SERM may be a partial agonist. Still another particular SERM may bind to ER and produce a molecular and/or cellular response that is only slightly less in magnitude than the response produced by estrogens. Such a SERM would result in a molecular and/or cellular response of a greater magnitude than the response produced by a partial agonist, but would not be referred to as an agonist because the molecular and/or cellular response is less than that produced by an agonist, like estrogen.

Chemically, SERMs can be classified into three groups (Osborne, et al., 2000, J Clin Oncol, 18:3172-86). The first group comprises triphenylethylene derivatives, of which TOT is one. Other substances that are triphenylethylene derivatives are toremifene, droloxifene (3-hydroxytamoxifen), idoxifene, TAT-59 (a phosphorylated derivative of 4-hydroxytamoxifen) and GW5638 (a carboxylic acid derivative of tamoxifen). The second group of SERMs comprises other nonsteroidal compounds. This group comprises EM-800, EM-652 (benzopyran), raloxifene, LY353381 (SERM 3) and LY357489. The third group of SERMs comprises steroidal compounds that have a better ability to inhibit the response produced by estrogens. ICI182,780 (ICI) is a member of this third group. The listings of substances that comprise each group is not complete and others may exist.

With regard to TOT, while it is effective in preventing proliferation of ER-positive breast tumor cells (i.e., cells that contain ER) in the early stages of breast cancer treatment, such ER-positive tumor cells invariably develop resistance to TOT. That is, after a time (e.g., 5 years), TOT is no longer effective in preventing estrogen stimulation of tumor proliferation and, in fact, causes stimulation of proliferation of ER-positive tumor cells. This TOT-resistant phenotype of breast tumor cells cannot be attributed solely to a decrease or absence of ER expression in the cells since more that 70% of TOT-resistant tumors continue to express ER (Crawford, et al., 1987, Br J Cancer, 56:137-40; Li, et al., 1994, J Surg Oncol, 57:71-7).

There is a need to understand the mechanism by which cells respond to and become resistant to SERMs. There is particular need to understand how ER-positive tumor cells become resistant to the proliferation inhibiting effects of TOT. Understanding the mechanism of TOT resistance, for example, would provide methods for identifying, and perhaps for predicting which cells will become resistant to TOT. Understanding the mechanism of TOT resistance can also provide substances that inhibit development of TOT resistance. Such methods and substances can be used to enhance the beneficial effects and reduce the side effects of TOT therapy.

SUMMARY OF THE INVENTION

In accordance with the present invention, it has been discovered that certain proteins, called "coregulator proteins," can bind to the ER, the ER already being bound by an antagonist, a partial agonist, or even an agonist, and cause the ER to become activated such that a molecular and/or cellular response is produced. Such coregulator proteins therefore, cause receptor ligands that alone can produce a variety of responses (antagonism, partial agonism, agonism) when bound to a receptor, to activate that receptor and produce a molecular and/or cellular response where one was not produced before (e.g., in the case of an antagonist), or to increase the magnitude of the molecular and/or cellular response produced (e.g., in the case of partial agonists and agonists). The coactivator protein referred herein is referred to as "Estrogen Receptor Coregulator 3" (ERCoA3). Because of its effects, ERCoA3 may play a role in development of resistance of tumor cells to antitumor compounds, such as TOT for example.

Therefore, the present invention relates to ERCoA3 proteins which interact with the estrogen receptor and the progesterone receptor and which cause activation of these receptors. ERCoA3 does the following: i) causes antagonists of ER (e.g., ICI182,780) to activate the receptor and produce an agonist or partial agonist activity, ii) causes partial agonists of ER (e.g., TOT) to increase the magnitude of their response on the receptor and, iii) causes agonists of ER (e.g., estrogens) to increase the magnitude of their response on the receptor. In addition ERCoA3: i) interacts with progesterone receptors (PR), when no ligand is bound to the receptor, and causes receptor activation (i.e., ERCoA3 acts as an agonist of PR) and, ii) causes partial agonists of PR (e.g., RU-486) to increase the magnitude of their response on the receptor.

The present invention provides purified ERCoA3 proteins, and biologically and/or immunologically reactive fragments thereof. In one embodiment, the purified ERCoA3 protein has the amino acid sequence shown in FIG. 2 (SEQ. ID. NO. 2). In another embodiment, the purified proteins are peptides from (i.e., parts of) SEQ. ID. NO. 2. In another embodiment, the protein, or peptides, have amino acid sequences that, while not identical to SEQ. ID. NO. 2 or parts thereof, are closely identical. In accordance with the present invention, it has been shown that ERCoA proteins are expressed at elevated levels in TOT-resistant cancer cell lines, enhance the transcriptional activation of the estrogen receptor (ER) by transhydroxytamoxifen (i.e., TOT) and cause transcriptional activation of ER when bound by the antagonist ICI182,780 (ICI). ERCoA3 proteins and fragments are also useful for making antibodies immunoreactive with ERCoA3 protein.

The present invention also provides isolated polynucleotides or nucleic acid molecules, which encode ERCoA3 or a portion thereof. In one aspect the isolated polynucleotides have the sequence shown in FIG. 1 (SEQ. ID. NO. 1). Such polynucleotides can be used to produce ERCoA3 protein. Such polynucleotides can also be used as probes for identifying cells that express ERCoA3 and quantifying expression of ERCoA3 in those cells. In another aspect, the isolated polynucleotides encode a part of the sequence shown in FIG. 1. Such polynucleotides can be used as probes and also as primers, for use in polymerase chain reactions (PCR) for example.

In still another aspect, the isolated polynucleotides or nucleic acid molecules encode a sequence complementary to all or part of the sequence shown in FIG. 1. Such polynucleotides can be used as probes or primers. Such polynucleotides can also be used as antisense polynucleotides. Antisense polynucleotides are useful for inhibiting expression of ERCoA3 genes.

The present invention also provides antibodies cross reactive to or immunospecific for the ERCoA3 protein, fragments or epitopes derived therefrom. Also encompassed are hybridoma cells and cell lines that produce such monoclonal antibodies immunospecific for ERCoA3 protein. Such antibodies can be polyclonal antibodies or monoclonal antibodies. The antibody may further comprise a detectable label, such as a fluorescent label, a chemiluminescent label, a radiolabel or an enzyme. Such antibodies are useful for identifying tissues with elevated levels of ERCoA, particularly tumor tissues comprising cells that are resistant to the proliferation inhibiting effects of TOT.

The present invention also provides methods for inhibiting the activity of ERCoA3. In one aspect, such method comprises introducing into cells a polynucleotide The present invention also provides methods for enhancing the activity of ERCoA3 in cells. In one aspect, such method comprises introducing into cells a polynucleotide comprising a sequence which encodes ERCoA. In one embodiment, the ERCoA3-encoding polynucleotides are encoded within a recombinant vector which comprises sequences permitting expression of the antisense polynucleotide in a target cell. In another aspect, the method for enhancing activity of ERCoA3 comprises introducing into cells ERCoA3 protein molecules. Such molecules may have attached to them, additional amino acids that facilitate uptake of the protein into the cells. Such methods for enhancing the activity the activity of ERCoA3 may be useful for treating diseases or conditions in which receptors, particularly ER, are decreased or less active than normal. One such condition is osteoporosis in post-menopausal women.

BRIEF DESCRIPTION OF THE FIGURES

FIG. 1. DNA sequence of ERCoA3 (SEQ. ID. NO. 1). The ATG start codon for the open reading frame is indicated in bold type and underlined. The TAA stop codon for the open reading frame is also indicated in bold type and underlined.

FIG. 2. Amino acid sequence of protein encoded by ERCoA3 (SEQ. ID. NO. 2).

FIG. 3. Pictures of transfected MCF-7 cells taken under a fluorescent microscope. Cells were transfected with 100 ng of pEGFP-ERCoA3 (ERCoA3 expression vector; left) or pEGFP-PCMT (a known non-nuclear protein; right). The cells were glycerol shocked and observed under a microscope 24 h later. For fluorescence image, fluorescein filters were used. Original images are at 400× total magnification. The pictures show that ERCoA3 protein is localized throughout the cells.

FIG. 6. ERCoA3 attenuates the antiestrogenic effects of TOT and ICI on ERα transcriptional activity. MCF-7 cells were transfected with (ERE)$_2$-PS2-CAT reporter construct. The cells were cotransfected with cmv5 control expression vector or expression vector for ERCoA3, as indicated. The cells were also transfected with a β-galactosidase internal control reporter to correct for transfection efficiency. Cells were then treated for 24 h with $10^{-8}$ M estradiol (E2) and increasing concentration of trans-hydroxytamoxifen (TOT; panel A) or ICI 182,780 (ICI; panel B). Values are the means±S.E. from three separate experiments.

FIG. 9. Antisense ERCoA3 results in decreased breast cancer cell growth. MCF-7 cells were infected with (A) antisense ERCoA3 retroviruses or (B) control retroviruses, in the presence or absence of tetracycline. Five days after infection phase contrast images were taken.

DETAILED DESCRIPTION OF THE INVENTION

Definitions

Herein, "antibody" means a protein molecule that binds to, cross reacts with, or is immunoreactive with a specific antigen or immunogen. The binding reaction between an antibody and its antigen is specific in that the antibody binds only to an amino acid sequence present within the specific protein (i.e., an epitope). Herein, an antibody against ERCoA3, also called an ERCoA3-specific antibody or an ERCoA3 antibody, will bind only to ERCoA3 proteins, or proteins that contain the same epitope.

Herein, "tumor" refers to a spontaneous, new growth of tissue in the body that forms an abnormal mass. Tumors are comprised of cells and such cells are known as tumor cells. Tumors and cells derived from tumors can be either benign or malignant (see below). "Neoplasm" is essentially synonymous with tumor.

Herein, "cancer" refers to a malignant tumor or neoplasm. Cells that are malignant have a variety of properties that benign cells and non-tumor cells do not have. Malignant cells invade, grow and destroy adjacent tissue, metastasize, and usually grow more rapidly than benign tumor cells.

Herein, "breast cancer" means any of various malignant neoplasms of the breast or mammary tissue.

Herein, "biological sample" means a sample of mammalian cells. These cells may be part of a tissue or organ sample obtained, for example, by biopsy, or they may be individual cells, for example, blood cells or cells grown in culture. Such samples may be of normal cells, or may be of tumor cells, the tumor cells being benign or malignant. Generally, an assay that uses cells from such biological samples, herein, will be used to determine the presence of or levels of ERCoA3 proteins or RNA transcripts. When such an assay is performed, the "test sample" will generally be a sample for which the presence or level of ERCoA3 is unknown and is being tested to provide, for example, an indication as to whether tumor cells are or are likely to become resistant to the proliferation inhibiting activity of TOT. In such an assay, a "control sample" will be used. The control sample can be from normal (i.e., non-tumorigenic or non-neoplastic) tissue. Cells from such control tissue samples will have relatively low or nonexistent levels of ERCoA3.

Herein, "proliferation" means growth and reproduction; i.e., division of cells.

ERCoA3 Background

The sequence of the ERCoA3 cDNA (SEQ. ID. NO. 1) is shown in FIG. 1. The amino acid sequence of the protein encoded by this cDNA, the 79 amino acid ERCoA3 protein (SEQ. ID. NO. 2), is shown in FIG. 2. Introduction of the ERCoA3 cDNA into cultured cells and overexpression of the ERCoA3 protein therein, shows that the protein is localized both in the nucleus and cytoplasm of the cell (FIG. 3).

Figure 4:
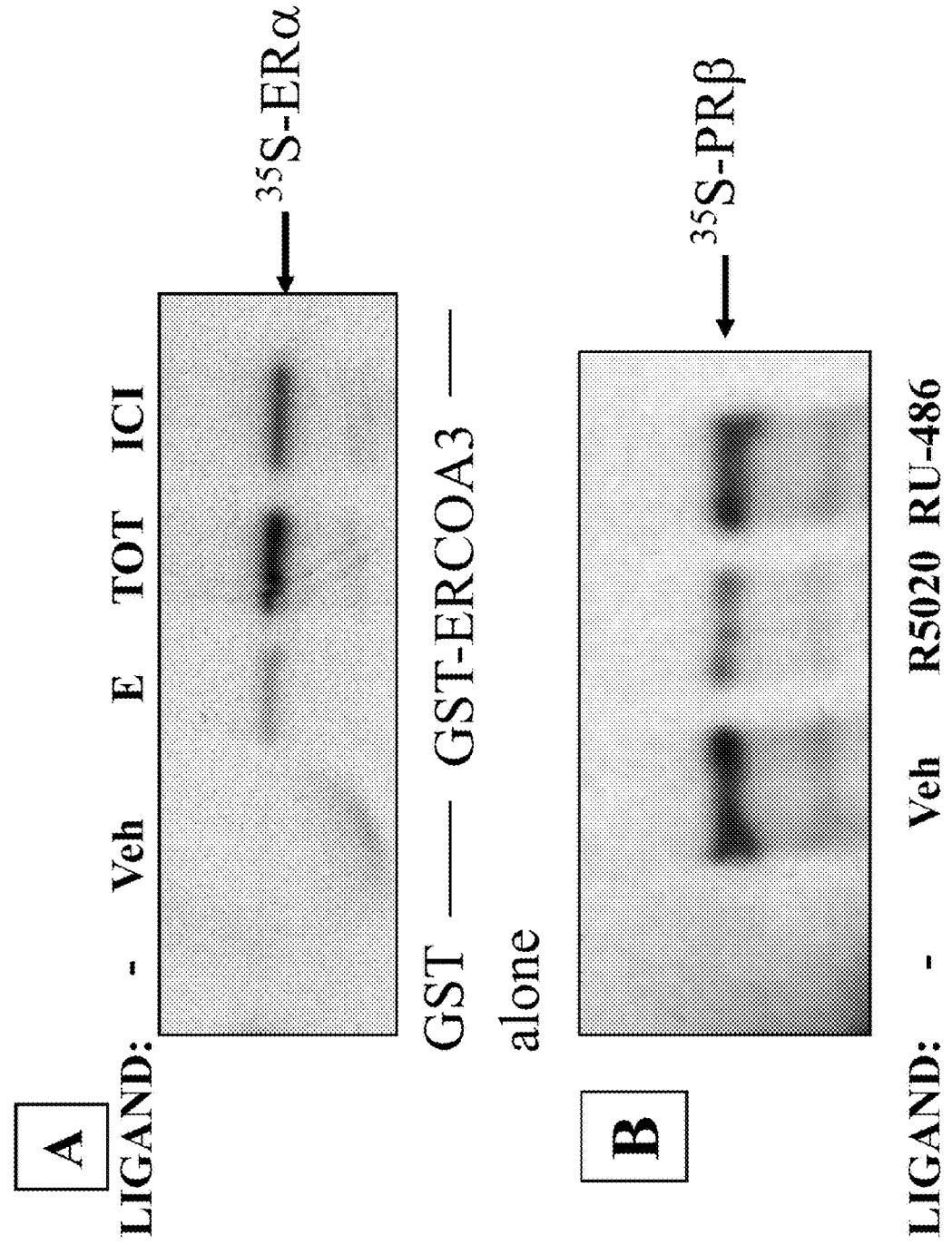
FIG. 4. ERCoA3 preferentially interacts with antagonist-bound ERα and PRβ. In vitro translated and [$^{35}$S]-methionine-labeled (A) Estrogen Receptor α (ERα) or (B) Progesterone Receptor β (PRβ) were incubated with GST alone or GST-ERCoA3 bound to Sepharose in the presence of vehicle, $10^{-6}$ M Estradiol ($E_2$), $10^{-6}$ M trans-hydroxytamoxifen (TOT), $10^{-6}$ M ICI 182,780 (ICI), $10^{-6}$ M R5020, or $10^{-6}$ M RU-486 as indicated. Bound protein was eluted with excess glutathione and analyzed by 12.5% SDS-polyacrylamide gel electrophoresis. The autoradiograph is representative of 3 separate experiments. Abbreviations: E2, 17-β estradiol; TOT, transhydroxytamoxifen; ICI, ICI182,780 (a pure ER antagonist); R5020, a synthetic PR agonist, and RU-486, a partial agonist of PRβ.

Direct interaction between the ERCoA3 protein and the estrogen receptor α (ERα) was demonstrated in in vitro studies. A protein-protein interaction assay was used in which the affinity matrix (i.e., bound to a column) was a glutathione-S-transferase (GST) fusion protein wherein GST was fused to ERCoA3. In vitro transcribed and translated [$^{35}$S]-ERα was retained by the GST-ERCoA3 affinity column preferentially in the presence of antiestrogens, trans-hydroxytamoxifen (TOT) and ICI182,780 (ICI) when compared to estradiol ($E_2$) (FIG. 4A). ERα was not retained on the GST protein column without ERCoA3 (or GST alone). These data show that ERCoA3 binds ER but binds ER better if ER are already bound to a partial agonist or antagonist.

Figure 5:
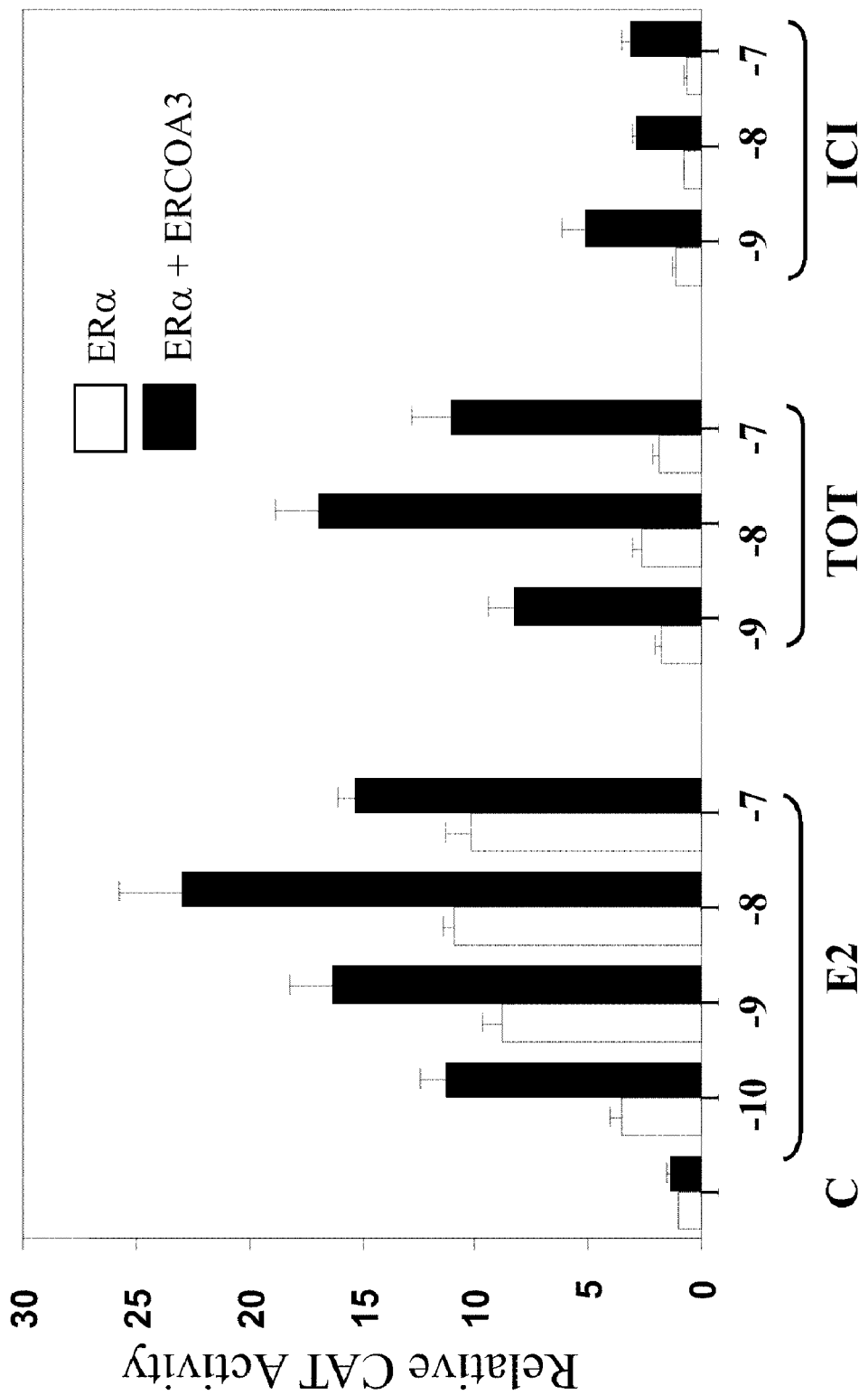
FIG. 5. ERCoA3 enhances partial agonist activity of antiestrogens. CHO cells were transfected with expression vectors for ERα and reporter construct (ERE)$_2$-TATA-CAT. The cells were cotransfected with cmv5 control expression vector or expression vector for ERCoA3, as indicated. The cells were also transfected with a β-galactosidase internal control reporter to correct for transfection efficiency. Cells were then treated for 24 h with control vehicle or increasing concentrations of estradiol ($E_2$), trans-hydroxytamoxifen (TOT) or ICI 182,780, as indicated. Values are the means±S.E. from three separate experiments.

The ability of ERCoA3 to affect the response that a ligand has on ER was then tested. CHO cells were transfected with a CAT reporter construct wherein transcription of the CAT gene was regulated by a estrogen-responsive element, or with both a CAT reporter construct and an expression vector for ERCoA3. The cells were grown in either estrogen, TOT or ICI, and CAT activity was assayed. The data (FIG. 5) show that ERCoA3 increased CAT activity, and therefore activation of ER in the presence of estrogen (an agonist), TOT (a partial agonist), and ICI (an antagonist).

Another very similar study examined the effect of ERCoA3 on the ability of TOT (FIG. 6A) and ICI (FIG. 6B) to block activation of ER. MCF-7 cells were transfected with a CAT reporter construct wherein transcription of the CAT gene was regulated by a estrogen-responsive element, or with both a CAT reporter construct and an expression vector for ERCoA3. The cells were then grown in TOT or ICI and CAT activity was assayed. The data show that ERCoA3 increases activation of ER (and, therefore, reverses the inhibitory effect of TOT and ICI on ER activation) over a wide concentration range of both TOT and ICI.

Figure 7:
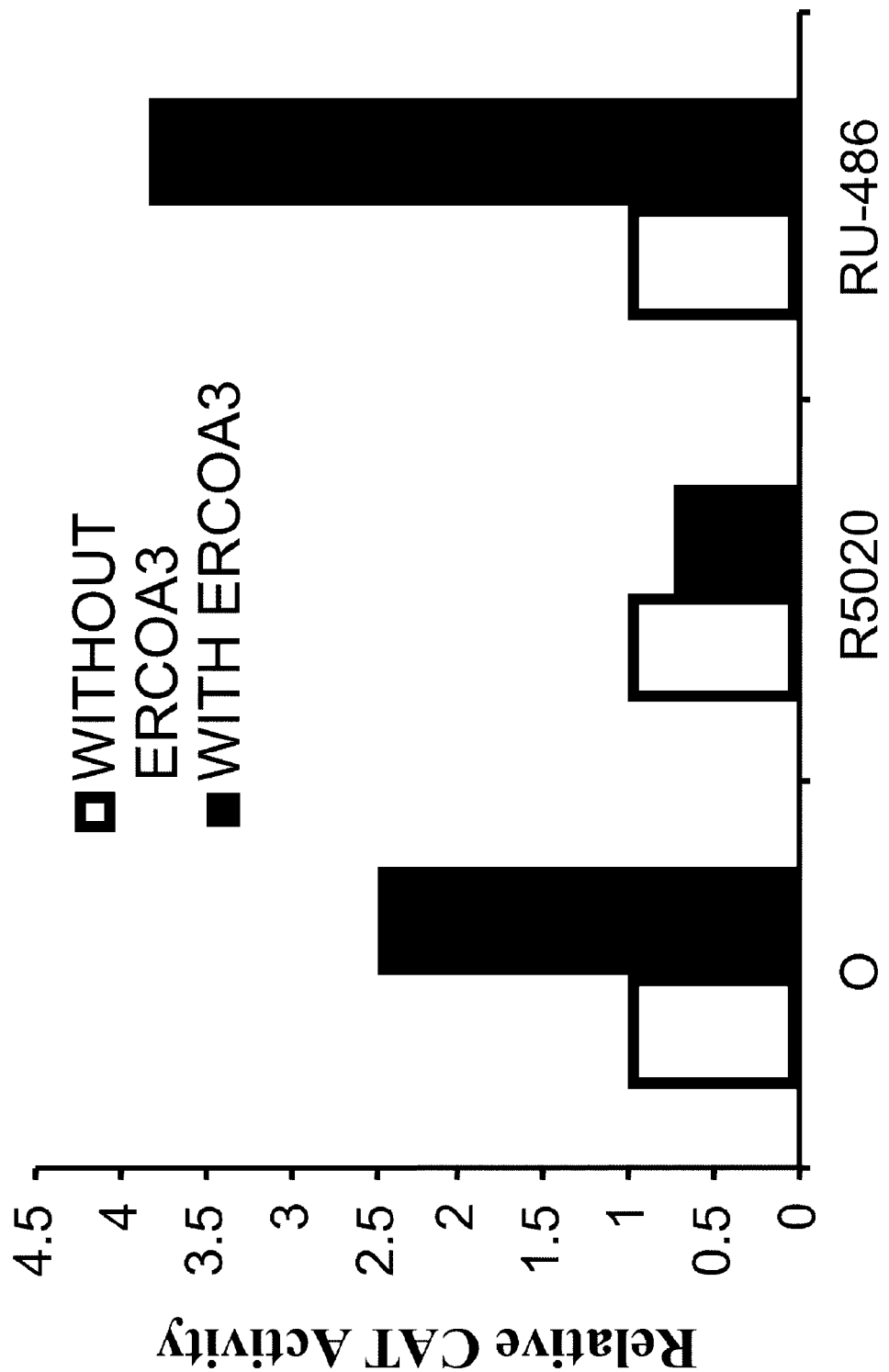
FIG. 7. ERCoA3 enhances partial agonist activity of RU-486. CHO cells were transfected with expression vectors for Progesterone Receptor β (PRβ) or reporter construct MMTV-CAT. The cells were cotransfected with cmv5 control expression vector or expression vector for ERCoA3 as indicated. The cells were also transfected with a β-galactosidase internal control reporter to correct for transfection efficiency. Cells were then treated for 24 h with $10^{-8}$ M R5020 or RU-486. Values are the means±S.E. from three separate experiments.

Somewhat different findings were made with Progesterone Receptor β (PRβ). ERCoA3 interacted with both unliganded and antiprogestin-(RU-486, a partial agonist) bound PRβ (FIG. 4B). This is reflected in the regulation of PRβ transcriptional activity (i.e., activation) wherein ERCoA3 enhanced the activity of both unliganded and RU-486-bound PRβ (FIG. 7).

Figure 8:
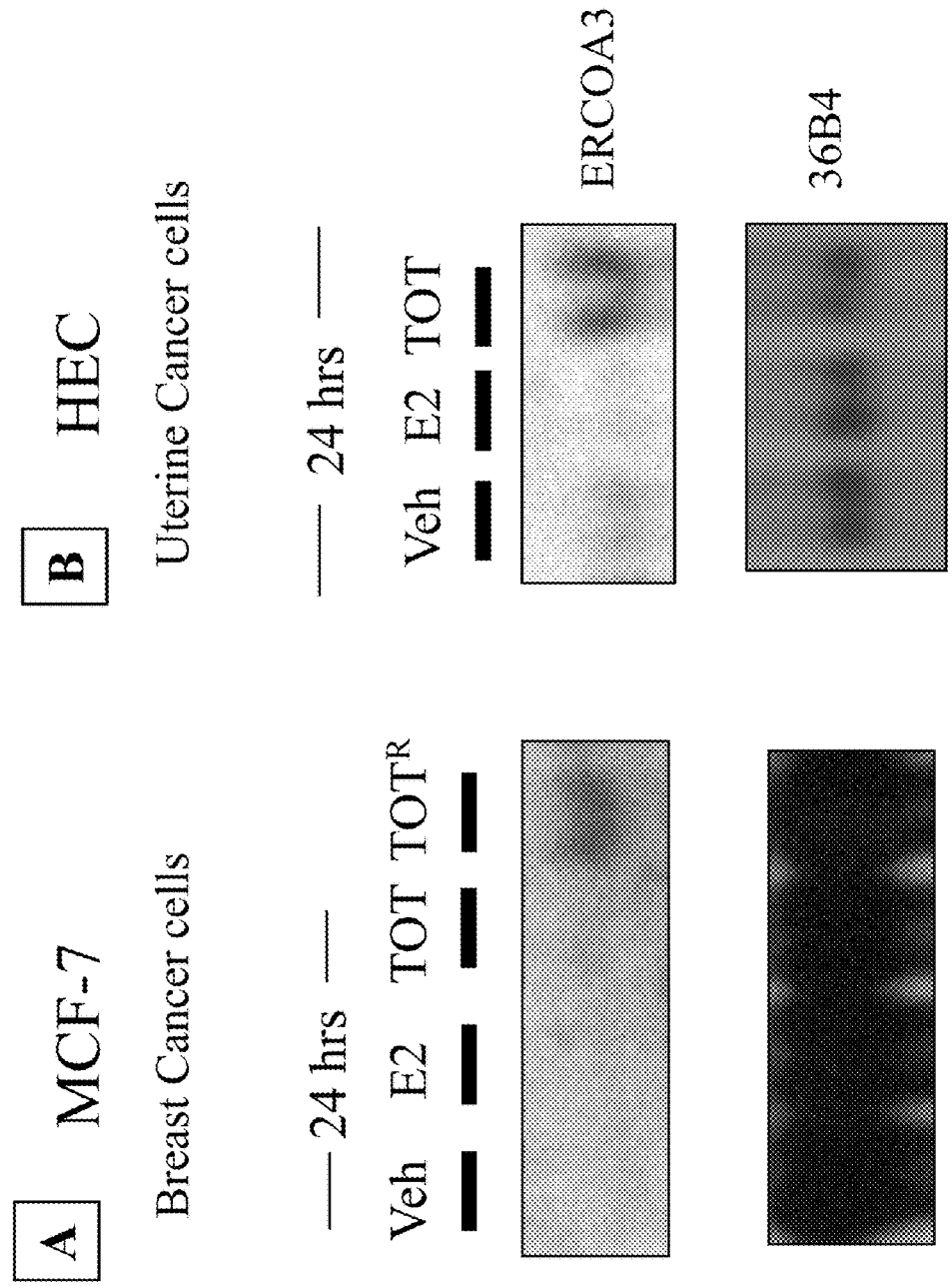
FIG. 8. ERCoA3 is expressed in cells that respond to tamoxifen as an agonist. (A) Total RNA was isolated from untreated parental MCF-7 cells (−), and cells treated for 24 h with $10^{-8}$ M estradiol ($E_2$) or $10^{-8}$ M trans-hydroxytamoxifen (TOT), and tamoxifen resistant cells (TOT$^R$). (B) Total RNA was collected from untreated Hec cells and cells treated for 24 h with $10^{-8}$ M estradiol ($E_2$) or $10^{-8}$ M trans-hydroxytamoxifen. Equal amounts (20 μg) of total RNA were separated by electrophoresis. Blots were probed with the random primer labeled ERCoA3 cDNA and 36B4 cDNA (to control for RNA loading).

It was determined whether there was increased expression of ERCoA3 in cells that were resistant to SERMs, specifically TOT. RNA was isolated from MCF-7 cells and also from tamoxifen-resistant (TOT$^R$) MCF-7 cells. Northern hybridization was performed using an ERCoA3 probe. These experiments indicated increased expression of ERCoA3 in TOT$^R$ MCF-7 cells when compared to parental MCF-7 cells (FIG. 8A). Neither E2 nor TOT affected ERCoA3 expression. Expression of ERCoA3 was also examined in another human cell line, human endometrium cancer cell line, HEC-1B. Tamoxifen shows high partial agonistic activity in HEC-1B cells. Tamoxifen induced expression of ERCoA3 in HEC-1B cells (FIG. 8B).

Thus, a novel ER coactivator, ERCoA3, with the following characteristics has been discovered: (1) interacts with or binds to agonist-ER complex, (2) interacts with antagonist-ER complex, (3) interacts with partial agonist-ER complex, (4) interacts with unliganded progesterone receptor (PR; unliganded means PR not bound to an agonist, partial agonist or antagonist), (5) interacts with agonist-PR complex and, (6) interacts with partial agonist-PR complex.

The ERCoA3 coactivator has the following functions: (1) causes agonists of ER (e.g., estrogens) to increase the magnitude of ER activation that they cause, (2) causes antagonists of ER (e.g., ICI182,780) to activate the receptor and produce an agonist or partial agonist activity, (3) causes partial agonists of ER (e.g., TOT) to increase the magnitude of their ER activation, (4) activates PR, and (5) causes partial agonists of PR (e.g., RU-486) to increase the magnitude of PR activation that they cause.

Significantly, when ERCoA3 causes antagonists to activate ER or causes agonists to increase activation of ER, ERCoA3 is also causing a decrease in the ability of the antagonist (e.g., ICI) or partial agonist (e.g., TOT) to inhibit growth proliferation resulting from activation of ER by estrogens. The data showing that breast and uterine cancer cell lines have higher than normal ERCoA3 levels (FIG. 8) indicates that ERCoA3 may play a role in acquisition of resistance of cancer cells to therapeutic agents (e.g., TOT)

ERCoA3 Proteins

The present invention provides human ERCoA proteins. In a preferred embodiment, the ERCoA3 protein is the sequence shown in FIG. 2 (SEQ. ID. NO. 2). The present invention also provides proteins that are structural variants of SEQ. ID. NO. 2, but are functional equivalents of the protein shown in SEQ. ID. NO. 2. Such functional equivalents have an altered sequence in which one or more of the amino acids in the corresponding reference sequence (SEQ. ID. NO. 2) is substituted, or in which one or more amino acids are deleted from or added to the corresponding reference sequence. The protein can be any variation of the amino acid sequence shown in FIG. 2, or can be shorter or longer than the sequence shown in FIG. 2, as long as the protein retains the ability to bind to a partial agonist bound to a receptor, or an antagonist bound to a receptor, and retains the ability to enhance the agonist activity thereof.

While it is possible to have nonconservative amino acid substitutions, it is preferred that, except for the substitutions that are made to replace cysteine, the substitutions be conservative amino acid substitutions, in which the substituted amino acid has similar structural or chemical properties with the corresponding amino acid in the reference sequence. By way of example, conservative amino acid substitutions involve substitution of one aliphatic or hydrophobic amino acids, e.g., alanine, valine, leucine and isoleucine, with another; substitution of one hydroxyl-containing amino acid, e.g., serine and threonine, with another; substitution of one acidic residue, e.g., glutamic acid or aspartic acid, with another; replacement of one amide-containing residue, e.g., asparagine and glutamine, with another; replacement of one aromatic residue, e.g., phenylalanine and tyrosine, with another; replacement of one basic residue, e.g., lysine, arginine and histidine, with another; and replacement of one small amino acid, e.g., alanine, serine, threonine, methionine, and glycine, with another.

Preferably, the deletions and additions are located at the amino terminus, the carboxy terminus, or both, of one of the sequences shown above. As a result of the alterations, the functional variant has an amino acid sequence which is at least 85% identical, preferably at least 90% identical, more preferably at least 95% identical, most preferably, at least 99% identical to the corresponding reference sequences. Sequences which are at least 90% identical have no more than 1 alteration, i.e., any combination of deletions, additions or substitutions, per 10 amino acids of the reference sequence. Percent identity is determined by comparing the amino acid sequence of the variant with the reference sequence using MEGALIGN project in the DNA STAR program.

The ERCoA proteins, and functional equivalents thereof, may be produced by conventional peptide synthesizers. The ERCoA proteins may also be produced using cell-free translation systems and RNA molecules derived from DNA constructs that encode the ERCoA proteins. Alternatively, ERCoA proteins are made by transfecting host cells with expression vectors that comprise a DNA sequence that encodes the respective ERCoA protein and then inducing expression of the protein in the host cells. For recombinant production, recombinant constructs comprising one or more of the sequences which encode the ERCoA protein are introduced into host cells by conventional methods such as calcium phosphate transfection, DEAE-dextran mediated transfection, transvection, microinjection, cationic lipid-mediated transfection, electroporation, transduction, scrape loading, ballistic introduction or infection.

The ERCoA proteins, and functional equivalents thereof, may be expressed in suitable host cells, such as for example, mammalian cells, yeast, bacteria, or other cells under the control of appropriate promoters using conventional techniques. Following introduction of DNA into the suitable host strain and growth of the host strain to an appropriate cell density, the cells are harvested by centrifugation, disrupted by physical or chemical means, and the resulting crude extract retained for further purification of the ERCoA protein.

Conventional procedures for isolating recombinant proteins from transformed or transfected host cells, such as isolation by initial extraction from cell pellets or from cell culture medium, followed by salting-out, and one or more chromatography steps, including aqueous ion exchange chromatography, size exclusion chromatography steps, high performance liquid chromatography (HPLC), and affinity chromatography may be used to isolate recombinant ERCoA protein. Such methods are well known to those skilled in the art.

The ERCoA3 proteins, and functional equivalents thereof, and immunological cross-reactive fragments, can be used for making antibodies.

ERCoA3 Polynucleotides

The present invention provides isolated polynucleotides (i.e. the ERCoA polynucleotides) which encode the ERCoA protein (FIG. 1; SEQ. ID. NO. 1) or isolated polynucleotides that encode structural variants that are functional equivalents of that protein, as described above. The ERCoA polynucleotides may be single-stranded or double stranded. Such polynucleotides may be DNA or RNA molecules. In certain embodiments, the ERCoA3 polynucleotide comprises the peptide coding sequence shown in FIG. 1.

The present invention also encompasses isolated polynucleotides which are alleles of the genes which encode the ERCoA proteins. As used herein, an allele or allelic sequence is an alternative form of the gene which may result from one or more mutations in the sequences which encode the ERCoA proteins. Such mutations typically arise from natural addition, deletion of substitution of nucleotides in the open reading frame sequences Any gene may have none, one, or several allelic forms. Such alleles are identified using conventional techniques, such as for example screening libraries with probes having sequences identical to or complementary with one or more ERCoA polynucleotides.

The present invention also encompasses altered polynucleotides which encode ERCoA proteins or ERCoA protein variants. Such alterations include deletions, additions, or substitutions. Such alterations may produce silent changes and result in an ERCoA protein having the same amino acid sequence as the ERCoA protein encoded by the unaltered polynucleotide. Such alterations may produce a nucleotide sequence possessing non-naturally occurring codons. For example, codons preferred by a particular prokaryotic or eucaryotic host may be incorporated into the nucleotide sequences shown in FIG. 1 to increase the rate of expression of the proteins encoded by such sequences. Such alterations may also introduce new restriction sites into the sequence or result in the production of a ERCoA protein variant. Typically, such alterations are accomplished using site-directed mutagenesis.

The polynucleotides that encode ERCoA3 proteins, or variants, or alleles, or altered polynucleotides thereof, as described above, are useful for expressing (i.e., making) the ERCoA3 proteins or variants. Use of the polynucleotides to express ERCoA3 proteins or variants can be performed using the methods described above, comprising cell-free translation systems or expression of the polynucleotides in various host cells, as described above. The ERCoA3 proteins that are expressed in the cells can then be isolated from the cells, using protein purification techniques, as described above. Alternatively, expression of ERCoA3 proteins in cells, using isolated polynucleotides and various gene transfer vectors, can be used to affect gene expression (either enhance or repress) in cultured cells or even in tissues of an organism. Such methods and uses thereof are described further later in this application.

As used herein, the term ERCoA polynucleotide also encompasses polynucleotides that hybridize under stringent conditions to the protein coding sequences shown in FIG. 1 and their variants, alleles and altered sequences or to the complement thereof. Such polynucleotides are useful tools for designing hybridization probes for isolating and identifying cDNA clones and genomic clones encoding the ERCoA genes or allelic forms thereof. Such polynucleotides are also useful for detecting transcripts from the genes which encode ERCoA3 proteins, for example, in Northern blotting experiments. Such hybridization techniques are known to those of skill in the art.

The term "stringent conditions, as used herein, is the "stringency" which occurs within a range from about $T_m-5$ (5° below the melting temperature of the probe) to about 20° C. below $T_m$. As used herein "highly stringent" conditions employ at least 0.2×SSC buffer and at least 65° C. As recognized in the art, stringency conditions can be attained by varying a number of factors such as the length and nature, i.e., DNA or RNA, of the probe; the length and nature of the target sequence, the concentration of the salts and other components, such as formamide, dextran sulfate, and polyethylene glycol, of the hybridization solution. All of these factors may be varied to generate conditions of stringency which are equivalent to the conditions listed above.

The probes are used in Northern assays to detect transcripts of ERCoA homologous genes and in Southern assays to detect ERCoA homologous genes. The identity of probes which are 200 nucleotides in length and have full complementarity with a portion of the antisense strand of a double-stranded DNA molecule which encodes ERCoA proteins is determined using the nucleotide sequence shown in FIG. 1 or portions thereof.

The present invention also provides for oligonucleotides that encode part of the sequence SEQ. ID. NO. 1, shown in FIG. 1, or part of the sequence of aforementioned variants, alleles and altered ERCoA3 sequences. Oligonucleotides can contain as few as 8 consecutive nucleotides of such sequences, all the way up to approximately 500 or 600 nucleotides. Some such oligonucleotides are useful as hybridization probes for identifying clones and for detecting transcripts from genes which encode ERCoA3 or ERCoA3-related proteins, as described above. Preferably, such oligonucleotides for hybridization comprise at least 200 nucleotides, more preferably at least 230, most preferably from about 210 to 280 nucleotides.

Such oligonucleotides for hybridization, also called hybridization probes, have a sequence which is at least 90% complementary with a sequence contained within the sense The present invention also provides oligonucleotide primers which can be used in the polymerase chain reaction (PCR) for a variety of purposes. One use of such PCR primers is in identifying and isolating polynucleotides from cDNA libraries, for screening tissue samples, or for diagnostic purposes. Another use for such PCR primers is in reverse transcription-PCR reactions (RT-PCR). RT-PCR reactions, using the PCR primers of this invention, are useful for detecting RNA transcripts, or parts of RNA transcripts, encoded by ERCoA3 genes. For example, such an assay is used for determining if cells from a particular tumor are expressing ERCoA3 genes. Such an assay can also be used in a quantitative fashion to determine how much of the ERCoA3 transcript is present. RT-PCR comprises isolating and using RNA from a cell, for example, in a reverse transcriptase reaction wherein the RNA is reverse transcribed into DNA. The PCR primers of this invention are then added to the DNA from the reverse transcription reaction and the mixture is used in a PCR reaction.

Preferably, the PCR primers comprise 18-30 nucleotides, more preferably 19-25 nucleotides. Preferably, the primers have a G+C content of 40% or greater. Such oligonucleotides are at least 98% complementary with a portion of the DNA strand, i.e., the sense strand, which encodes the respective ERCoA family protein or a portion of its corresponding antisense strand. Preferably, the primer has at least 99% complementarity, more preferably 100% complementarity, with such sense strand or its corresponding antisense strand. Primers which have 100% complementarity with the antisense strand of a double-stranded DNA molecule which encodes a ERCoA family protein have a sequence which is identical to a sequence contained within the sense strand. The identity of primers which are 15 nucleotides in length and have full complementarity with a portion of the antisense strand of a double-stranded DNA molecule which encodes the ERCoA3 protein is determined using the nucleotide sequence or portions thereof shown in FIG. 1. Such methods are well known to those skilled in the art.

Such primers for PCR comprise a pair of set of primers. One primer of the pair is called the "forward primer" and is located at the left end of the sequence to be amplified. The second primer of is called the "reverse primer" and is located at the right end of the sequence to be amplified. The forward primer hybridizes to the opposite strand of the template (the DNA to be amplified) than does the reverse primers. Selection of forward and reverse primers, for the purpose of amplifying a sequence of DNA by PCR, is well known to one skilled in the art.

Examples of such primers for ERCoA3 include, but are not limited to:

```
ERC1: GGAATTGTTCTCGAGGCCAA    (SEQ. ID. NO. 3)

ERC2: AACTTGCGGCCGCTCATTTT    (SEQ. ID. NO. 4)
```

Such primers, when used in a PCR reaction with ERCoA3 DNA as template, result in amplification the DNA. Many other primers can be used to amplify ERCoA3 sequences, variants and alleles thereof. Herein, any such primers are encompassed within the present application. Methods for choosing PCR primers useful for amplifying a particular sequence are well known to those skilled in the art.

Also encompassed by the present invention, are single stranded polynucleotides, hereinafter referred to as antisense polynucleotides, having sequences which are complementary to the DNA, and especially RNA sequences, which encode the ERCoA protein, variants or alleles thereof. Such antisense polynucleotides can be either DNA or RNA. The term "complementary" as used herein refers to the natural binding of the polynucleotides under permissive salt and temperature conditions by base pairing (i.e., formation of hydrogen bonds). The meaning of the term "complementary," when referring to nucleic acids is well known in the art. Such antisense polynucleotides or oligonucleotides are designed, for example, to hybridize to the 5' end of the ERCoA3 gene or transcript derived therefrom.

Antisense polynucleotides are designed for the purpose of decreasing expression of a particular gene, in a cell for example. The concept is that, within a cell, an antisense polynucleotide or oligonucleotide hybridizes to its complement, which is either an RNA transcript from a specific gene, or one strand of the gene itself. When such hybridization occurs, the RNA transcript is unable to be translated into a protein, or the gene itself is unable to be transcribed into mRNA. In either case, expression of that specific gene, as measured by the amount of functional protein expressed, is decreased relative to the situation where no antisense polynucleotide or oligonucleotide has been used. As described above, the sequence of such antisense oligonucleotides is complementary to one DNA strand of the gene, or to the mRNA that is transcribed from the gene. Such antisense polynucleotides or oligonucleotides can be modified in ways known to those skilled in the art, such modification resulting in the polynucleotide or oligonucleotide having a longer half-life within a cell relative to the same polynucleotide or oligonucleotide that does not contain the modification. Antisense polynucleotides or oligonucleotides are introduced into cells in a variety of ways. Antisense polynucleotides can, for example, be put in contact with the exterior surface of a cell or cells within a tissue, in which case some or all of the cells will take up the antisense polynucleotides into the cell. Antisense polynucleotides can also be encoded in a gene transfer vector, for example. Introduction of the vector into a cell results in the vector being transcribed into RNA, one or more of the RNAs comprising the antisense polynucleotide.

Synthesis of Polynucleotides Encoding ERCoA Proteins or Variants Thereof

Polynucleotides comprising sequences encoding an ERCoA protein, variant or allele thereof may be synthesized in whole or in part using chemical methods. Such methods usually utilize automated instruments known as "oligonucleotide synthesizers." Oligonucleotide synthesizers and their methods of use are well known to those skilled in the art.

Polynucleotides which encode an ERCoA protein, particularly alleles of the genes which encode an ERCoA protein, may also be obtained by screening a genomic library or cDNA library with a probe comprising sequences identical or complementary to the sequences shown in FIG. 1, or with antibodies immunospecific for an ERCoA protein, to identify clones containing such polynucleotide.

The probes are used in Northern blot or colony hybridization assays under high stringency conditions. Alternatively, polynucleotides encoding ERCoA3 proteins may be made using polymerase chain reaction (PCR) technology and primers which bind specifically to sequences which are known to encode an ERCoA protein. These methods have been described above.

The ERCoA3 polynucleotides are useful for preparing ERCoA proteins. The ERCoA polynucleotides or fragments are also useful for identifying breast tumor cells whose proliferation is stimulated by tamoxifen therapy, i.e., breast tumor cells in which tamoxifen acts as an agonist rather than an antagonist, i.e. and the margins or borders tumors comprising such cells. Breast tumor cells whose proliferation is stimulated by tamoxifen have higher levels of ERCoA mRNA than breast tumor cells whose growth is inhibited by tamoxifen. Thus, ERCOa polynucleotides may be used as probes in Northern analysis to identify tumors which have comparatively lower and higher levels of ERCoA mRNA. In such procedures total RNA or mRNA is obtained from the tumor tissue and from normal breast epithelial cells preferably from the same patient, and then assayed using the ERCoA-designed probe. In general, the normal breast epithelial cells will be obtained from tissues adjacent to the border of the tumor. Similarly, ERCoA-designed primers may be used in RT-PCR to quantify the amount of ERCoA mRNA in tumor tissues.

Antibodies that React with ERCoA3 Protein

The present invention also provides antibodies that are immunospecific for the ERCoA3 protein. As used herein, the term "immunospecific" means the antibodies have greater affinity for the ERCoA protein than for other proteins, especially for other proteins found in breast epithelial cells.

The term "antibody" encompasses monoclonal antibodies, polyclonal antibodies, multispecific antibodies (e.g., bispecific antibodies), and antibody fragments, so long as they exhibit the desired biological activity or specificity. "Antibody fragments" comprise a portion of a full length antibody, generally the antigen binding or variable region thereof. Examples of antibody fragments include Fab, Fab', F(ab')$_2$, and Fv fragments.

Antibodies raised against ERCoA are produced by immunizing a host animal with an ERCoA protein or an antigenic fragment thereof. Suitable host animals for injection of the protein immunogen include, but are not limited to, rabbits, mice, rats, goats, and guinea pigs. Various adjuvants may be used to increase the immunological response of the immunogen or antigen (i.e., the ERCoA3 protein or peptide) in the host animal. The adjuvant used depends, at least in part, on the host species. For example, guinea pig albumin is commonly used as a carrier for immunizations in guinea pigs. Such animals produce heterogeneous populations of antibody molecules, which are referred to as polyclonal antibodies and which may be derived from the sera of the immunized animals. Such sera may be used directly, or the specific antibodies desired can be purified from the sera, using methods well known to those of skill in the art.

The term "monoclonal antibody" as used herein, refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site, also called epitope. Furthermore, in contrast to conventional (polyclonal) antibody preparations, which typically include different antibodies directed against different determinants (epitopes), each monoclonal antibody is directed against a single determinant on the antigen.

The monoclonal antibodies to be used in accordance with the present invention may be made by the hybridoma method, first described by Kohler and Milstein (Kohler and Milstein, 1975, Nature, 256:495-7), in which case the hybridoma cell lines that are obtained secrete the monoclonal antibodies during growth. In order to grow the hybridoma cell lines and obtain the secreted antibodies, the hybridoma cell lines may be grown in cell culture and culture medium containing the monoclonal antibodies collected. Alternatively, the hybridoma cell lines may be injected into, and grown within, the peritoneal cavity of live animals, preferably mice. As the hybridoma cell lines grow within the peritoneal cavity of the animal, the monoclonal antibodies are secreted. This peritoneal fluid, called "ascites," is collected using a syringe to obtain the monoclonal antibodies. Such antibodies may be of any immunoglobulin class including IgG, IgM, IgE, Iga, IgD and any class thereof.

Antibody preparations may be isolated or purified. An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody may be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step Antibodies immunospecific for ERCoA3 are useful prognostic markers for identifying breast cancers that are responsive, or conversely, refractive, to tamoxifen therapy. The diagnostic/prognostic method comprises the steps of contacting tumor cells and normal breast epithelial cells, with such antibody and assaying for the formation of a complex between the antibodies and a protein in the cell samples. Preferably the tumor cells and normal cells are permeabilized. Interactions between antibodies and a protein or peptide in the sample are detected by radiometric, calorimetric, or fluorometric means. Detection of the antigen-antibody complex may be accomplished by addition of a secondary antibody that is coupled to a detectable tag, such as for example, an enzyme, fluorophore, or chromophore. Formation of high levels of complex in the tumor cell as compared to the normal cells indicates that tamoxifen therapy is unlikely to be successful.

Methods of Inhibiting Tamoxifen-Induced Proliferation of Breast Cancer Cells, Endometrial Cells, and Uterine Cells Using Antisense ERCoA Polynucleotides The present invention also provides methods reducing levels of ERCoA3 transcripts and/or protein in the cells. Such methods are useful for inhibiting estrogen-induced (i.e., agonist) and tamoxifen-induced (i.e., partial agonist) proliferation of breast cancer cells, endometrial cells, and uterine cells in vitro and in vivo. In one embodiment, the method comprises expressing an antisense ERCoA polynucleotide in the target cell.

The antisense ERCoA3 polynucleotide (described above), typically, is introduced into the cell using a vector, such as a plasmid, or a viral vector. Preferably, expression of the antisense ERCoA3 polynucleotide or oligonucleotide within the cell is regulated by a tissue-specific promoter which is operably linked to the ERCoA antisense sequence within the vector. Alternatively, the antisense ERCoA is introduced into the cell using a liposome which, preferably, further comprises a targeting molecule for targeting delivery of the liposome and the ERCoA antisense polynucleotide to the desired target cell. The ERCoA antibody may also be introduced into the target cell via a targeted liposome.

Viral Vectors

Examples of known viral vectors are recombinant viruses which are generally based on various viral families comprising poxviruses, herpesviruses, adenoviruses, parvoviruses and retroviruses. Such recombinant viruses generally comprise an exogenous gene (herein, the ERCoA3 antisense polynucleotide) under control of a promoter which is able to cause expression of the exogenous gene in vector-infected host cells. Recombinant viruses which can be used to transfect cells are mentioned and cited, for example, in a review by Mackett, Smith and Moss (Mackett, et al., 1984, J Virol, 49:857-64).

Preferably, the virus vector is a defective adenovirus which has the exogenous gene (i.e., ERCoA3 antisense polynucleotide) inserted into its genome. The term "defective adenovirus" refers to an adenovirus incapable of autonomously replicating in the target cell. Generally, the genome of the defective adenovirus lacks the sequences necessary for the replication of the virus in the infected cell. Such sequences are partially or, preferably, completely removed from the genome. To be able to infect target cells, the defective virus must contain sufficient sequences from the original genome to permit encapsulation of the viral particles during in vitro preparation of the construct. Other sequences that the virus must contain are any such sequences that are said to be genetically required "in cis."

Preferably, the adenovirus is of a serotype which is not pathogenic for man. Such serotypes include type 2 and 5 adenoviruses (Ad 2 or Ad 5). In the case of the Ad 5 adenoviruses, the sequences necessary for replication are the E1A and E1B regions. Again, in a defective Ad 5 vector, one or both of these sequences are removed or mutated. Methods for preparing adenovirus vectors are described in U.S. Pat. No. 5,932,210, which issued in August, 1999 to Gregory et al., U.S. Pat. No. 5,985,846 which issued in November, 1999 to Kochanek et al, and U.S. Pat. No. 6,033,908 which issued in March, 2000, to Bout et al.

More preferably, the virus vector is an immunologically inert adenovirus. As used herein, the term "immunologically inert" means the viral vector does not encode viral proteins that activate cellular and humoral host immune responses. Methods for preparing immunologically inert adenoviruses are described in various articles, which are incorporated herein by reference (Parks, et al., 1996, Proc Natl Acad Sci USA, 93:13565-70; Lieber, et al., 1996, J Virol, 70:8944-60; Hardy, et al., 1997, J Virol, 71:1842-9; Morsy, et al., 1998, Proc Natl Acad Sci USA, 95:7866-71).

Some such methods involve Cre-loxP recombination. In vitro, Cre-loxP recombination is particularly adaptable to preparation of recombinant adenovirus and offers a method for removing unwanted viral nucleotide sequences. Replication-deficient recombinant adenovirus lacks the E1 coding sequences necessary for viral replication. This function is provided by 293 cells, a human embryonic kidney cell line transformed by adenovirus. First generation adenoviruses are generated by co-transfecting 293 cells with a helper virus and a shuttle plasmid containing the foreign gene of interest. This results in the packaging of virus that replicates both the foreign gene and numerous viral proteins. More recently, 293 cells expressing Cre recombinase, and helper virus containing essential viral sequences and with a packaging signal flanked by loxP sites, have been developed (Parks, et al., 1996, Proc Natl Acad Sci USA, 93:13565-70). In this system, the helper virus supplies all of the necessary signals for replication and packaging in trans, but is not packaged due to excision of essential sequences flanked by loxP. When 293-Cre cells are co-transfected with this helper virus, and a shuttle plasmid (pRP1001) containing the packaging signal, nonsense "filler DNA", and the foreign (antisense) gene, only an adenovirus containing filler DNA and the foreign gene is packaged (LoxAv). This results in a viral recombinant that retains the ability to infect target cells and synthesize the foreign gene, but does not produce viral proteins.

Methods of Inhibiting Tamoxifen-Induced Proliferation of Breast Cancer Cells, Endometrial Cells, and Uterine Cells Using ERCoA Antibodies In another embodiment the method comprises introducing an ERCoA antibody into the cell. Introduction of such antibodies can be performed either by introducing into the cells the antibody itself, or the gene or genes encoding the antibody molecule. Such antibodies comprise "intracellular antibodies" or "intrabodies" which are single-chain antibodies derived from monoclonal antibodies in which the variable domains of the light and heavy chains are joined together by a peptide linker (Mhashilkar, et al., 1995, Embo J, 14:1542-51).

Antibody molecules can be introduced into cells in a variety of ways known to those skilled in the art. One method is facilitated by adding to the antibody molecule, an amino acid sequence comprising a so-called "protein-transduction domain" (PTD) or "membrane transport signal" (MTS). Such domains or signals normally comprise 10-35 amino acids. Such PTD domains are derived from HIV-TAT, HSV-VP22 and Antenapedia, and are characterized by a high arginine and lysine content (Schwarze, et al., 2000, Trends Cell Biol, 10:290-5). Such MTS sequences are hydrophobic peptides derived from secretory signal sequences (Rojas, et al., 1998, Nat Biotechnol, 16:370-5; Rojas, et al., 1996, J Biol Chem, 271:27456-61).

These domains cause proteins that come in contact with the surface of cells, to be taken up by the cells such that the proteins are contained within the cell. In one embodiment, an eleven amino acid sequence, the PTD, from the human immunodeficiency virus TAT protein (Green and Loewenstein, 1988, Cell, 55:1179-88; Frankel and Pabo, 1988, Cell, 55:1189-93) is fused to the antibody. The purified antibody is then put in contact with the surface of cells and the cells take up the antibody which functions to inhibit ERCoA3 activity In the case where it is desired to introduce the antibody containing the fused PTD into cells comprising a tumor in a human or animal, the protein is administered to the human by a variety of methods. Preferably, the protein is administered by injection (e.g., intravenously) or by inhalation in an aerosol.

Antibodies that contain the fused PTD are preferably made by fusing the DNA sequence encoding the antibody, preferably intrabodies, with the DNA sequence encoding the PTD. The resulting antibody-PTD fusion gene is preferably incorporated into a vector, for example a plasmid or viral vector, that facilitates introduction of the fusion gene into an organism and expression of the gene at high levels in the organism such that large amounts of the antibody are made therein. One such organism in which the vector containing the fusion gene can be expressed is a bacterium, preferably *Escherichia coli*. Other organisms are also commonly used by those skilled in the art. After the fusion protein is expressed at a high level in any of these organisms, the fusion protein is purified from the organism using protein purification techniques well known to those skilled in the art.

Methods for Enhancing Agonist or Partial Agonist Activity of ER Ligands

The present invention also provides methods for enhancing the agonist or partial agonist activity of ER ligands, such as for example, estrogen or tamoxifen in cells. Such method can be performed by introducing into cells the ERCoA3 protein or variant or allele. Such method can also be performed by introducing into the cells, and overexpressing, a gene that encodes the ERCoA3 gene. These methods are performed in a way very similar to methods that have already been described in this application. Introduction of an ERCoA3 protein into cells, preferably using PTD or MTS domains, is done similarly to the method already described for introducing antibody molecules into cells. Introduction of genes encoding ERCoA3 into cells, preferably using viral vectors, is done similarly to the method already described for introducing ERCoA3 antisense molecules into cells.

The methods for introducing ERCoA3 proteins or genes encoding ERCoA3 proteins into cells can be used as a method for treating osteoporosis in post-menopausal women. Decreased production of estrogens, especially during menopause in females, can have a variety of effects on estrogen-sensitive tissues. One such effect is the progressive loss of mineral mass of bones and collagen over a period of years. Such loss of bone mass and collagen can result in osteoporosis. The loss of bone mass in osteoporosis causes deterioration of bones and an increased susceptibility to bone fracture.

Estrogen is an inhibitor of osteoclasts, a cell type that causes bone resorption. Lack of estrogen or estrogen activity causes increased activity of osteoclasts and, therefore, contributes to osteoporosis. By increasing the activity of estrogen or ER, the rate of progression of osteoporosis is slowed. One method of increasing the activation of ER is by increasing the levels of the ERCoA3 protein.

In this method, therefore, introduction of these proteins or genes encoding such proteins is performed similar to what has already been described. In one embodiment, the proteins or genes are introduced into osteoclasts.

Although the invention has been described with regard to a number of preferred embodiments, which constitute the best mode presently known to the inventors for carrying out this invention, it should be understood that various changes and modifications as would be obvious to one having the ordinary skill in this art may be made without departing from the scope of the invention which is defined by the claims which are appended hereto.

EXAMPLES

The invention may be better understood by reference to the following examples, which serve to illustrate but not to limit the present invention.

Example 1

Alteration of ERCoA3 Expression Affects Growth of Breast Cancer Cells

The functional relevance of ERCoA3 regulation of ERα activity was examined by assaying the consequence of changes in endogenous expression of ERCoA3 on estrogen-stimulated proliferation of breast cancer cells. A self-contained tetracycline-off retroviral vector system was used to inducibly overexpress or inhibit the expression of ERCoA3 in breast epithelial cell lines. MCF-7 cells were infected with either antisense ERCoA3 retroviruses (FIG. 9A) or control retroviruses (FIG. 9B) in the presence or absence of tetracycline. The data (phase contrast images taken 5 days after infection) showed that, after withdrawal of tetracycline, expression of antisense ERCoA3 induced a 50% decrease in endogenous ERCoA3 expression (data not shown) and caused inhibition of cell growth.

What is claimed is:

1. An isolated polypeptide comprising an amino acid sequence having at least 95% identity to the amino acid sequence set forth in SEQ ID NO: 2, wherein said isolated polypeptide binds antagonist-bound estrogen receptor-α, agonist-bound estrogen receptor-α or progesterone receptor β, and wherein the differences between the amino acid sequence of the polypeptide and SEQ ID NO: 2 are due to conservative amino acid substitutions.

2. The isolated polypeptide of claim 1, wherein said isolated polypeptide binds estradiol-bound estrogen receptor-α, trans-hydroxytamoxifen-bound estrogen receptor-α or ICI 182780-bound estrogen receptor-α.

3. An isolated polypeptide comprising the amino acid sequence set forth in SEQ ID NO: 2.

4. An isolated polypeptide consisting of the amino acid sequence set forth in SEQ ID NO: 2.

5. A composition comprising the isolated polypeptide of claim 1.

6. A composition comprising the isolated polypeptide of claim 3.

7. A composition comprising the isolated polypeptide of claim 4.

* * * * *